United States Patent [19]

Potin et al.

[11] Patent Number: 4,724,140

[45] Date of Patent: Feb. 9, 1988

[54] COMPOSITIONS FOR THE HYDRATION OF KERATINIC SUBSTANCES SUBSTITUTED BY ALPHA-AMINO ACID SULFOXIDES

[75] Inventors: Philippe Potin, Billere; Marie-Claude Martini, Lyons, both of France

[73] Assignee: Societe Nationale Elf Aquitaine (Production), France

[21] Appl. No.: 235,845

[22] Filed: Feb. 19, 1981

[30] Foreign Application Priority Data

Feb. 22, 1980 [FR] France ................................ 80 03894

[51] Int. Cl.[4] .......................... A61K 7/06; A61K 7/08; C07C 147/02; C07C 149/24
[52] U.S. Cl. ...................... 424/70; 514/844; 514/847; 562/556; 562/557
[58] Field of Search .................... 562/556, 557; 424/70

[56] References Cited

U.S. PATENT DOCUMENTS 2,049,480  8/1936  Toennies ............................... 562/557

FOREIGN PATENT DOCUMENTS 18-18893  8/1943  Japan ..................................... 562/556
2023003  12/1979  United Kingdom ................. 424/319

OTHER PUBLICATIONS

Toennies, Chem. Abs., 1939, vol. 33, pp. 1271, 5359, 5360.
Singal et al, Chem. Abs., vol. 35, 1941, pp. 6638 and 6639.
Kensaku, Chem. Abs., vol. 62, 1965, pp. 9229.
Journal of Org. Chem., 1958, vol. 23, No. 9, pp. 1251 to 1261, Goodman et al.

*Primary Examiner*—Dale R. Ore
*Attorney, Agent, or Firm*—Ostrolenk, Faber, Gerb & Soffen

[57] ABSTRACT

Compositions for the hydration of keratinic substances constituted by amino acid sulfoxides. A particular product is methionine sulfoxide. Important application in cosmetology where these products are incorporated in aqueous and organic solutions and oily or other emulsions. These products play a hydrating role in skin application and act as a softening agent on the hair.

6 Claims, No Drawings

COMPOSITIONS FOR THE HYDRATION OF KERATINIC SUBSTANCES SUBSTITUTED BY ALPHA-AMINO ACID SULFOXIDES

The present invention is related to products having hydrating properties with regard to keratin-containing substances, particularly skin, phaner, especially hair, body hair and other similar substances. In cosmetology, the importance of creams and ointments for hydrating the skin, thereby softening it, is currently known; hairdressings use, among other products, substances giving hair the desired softness.

Extensive research in these fields have established that one of the essential reasons for water-retention by the outer layer of the skin, is the presence in the layer itself of hydrophilic substances called "normal hydration factors"; among these factors contained in the outer layer may be cited: free amino acids; pyrrolidone; carboxylic acid; urea; uric acid; glucosamine; creatinine, lactic, citric, formic acids; sugars and various peptides; sodium, calcium, ammonium, potassium, magnesium, phosphate, and chloride ions.

Through their hydrophilic character, these substances fix the water between the keratin fibres that assure the outer skin layer structure. This results in the swelling and plastification of this layer thereby giving a favourable optical effect to the skin by smoothing it, and an improved feeling of comfort by rendering it softer.

In spite of the presence in the outer skin layer of these hydration factors, it can occur that certain persons react by drying of the skin, due to one of several causes; skin fragility, tough atmospheric conditions, deficiency of the organism to form the cited factors.

In order to overcome this drawback, and re-establish the correct hydrous balance of the skin, it is known that hydration factors may be added by the intermediary of creams to be applied to the skin, either by incorporating in a cream or lotion one or several previously described "hydration factors", or incorporating in the creams artificial hydration factors such as glycerine, propylene glycol, or sorbitol. Good results are obtained with carboxylate, pyrrolidone or sodium lactate but the effectiveness of all these substitution products does not always correspond to what is expected. Penetration of these products is often only partial. It also happens that certain products produce the opposite effect of dehydration by resting on the skin surface.

It was therefore necessary to find products which combined a good penetration power with a pronounced hydrophilic character.

The present invention is a result of the unexpected finding that certain amino acid sulfoxides bear three favorable properties, i.e. good solubility, good hydrating power and penetration in keratinic substance, thus making these hydration agents superior to those already known in the state of the art.

The novel hydration agents according to the present invention, are α-amino acid sulfoxides, represented by the following formula:

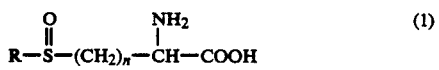

in which:
n is an integer of 1 to 4,
R being an organic group, able to contain one or several S, O and N atoms joined to carbon atoms.

More particularly, R is a $C_1$ to $C_6$ and more often $C_1$ to $C_4$ alkyl radical.

The R group may also have the following form:

or

Inter alia, R may be an amino acid grouping:

in which:
m, as in forms (2) and (3), may be any integer from 0 to 4, different from n or identical to the latter coefficient.

A particularly effective representative of the agents according to the present invention is compound (1) in which the R group is a methyl, n being 2, i.e. the methionine sulfoxide:

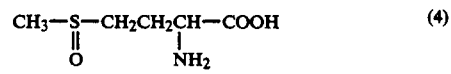

a body easily accessible on an industrial basis. The solubility of methionine sulfoxide in water (about 50%) being high, it is possible to prepare solutions or emulsions containing up to approximately 20% of this sulfoxide, whereas usually 5–10% solutions are sufficient for everyday needs. Methionine sulfoxide is very hydrophilic and has a strong affinity for keratin, thus allowing its deep penetration in skin or hair.

Methionine sulfoxide is totally toxic-free for the organism; data in the relevant literature and tests carried out show its total non-toxicity. On the other hand, this product is most effective when used in cosmetology. In fact, nutritional and biochemical studies carried out show that methionine is reduced "in vivo" and metabolised in the form of methionine which, itself, as is known, is not only totally toxic-free but, moreover, indispensable for the synthesis of proteins.

Homologues of compound (4), in which $CH_3$ is replaced by $C_2H_5$—, $C_3H_7$—, $C_4H_9$—, etc. bear similar properties.

The compounds according to formula (1) with n=1, may be obtained from cysteine:

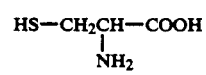

by alkylation on the HS— group, then sulfoxidation which produces alkyl sulfoxy-4 α-amino propionic acid

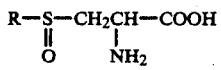

R being, as stated previously, $CH_3$—, $C_2H_5$— or generally $C_1$ to $C_6$ alkyl radicals.

Such methods of preparation are known in the art and there is thus no need to describe them here; it should be recalled, however, that the alkylation of cysteine may be carried out through the action of an alkyl halide in a basic medium or by photochemical addition of an olefin.

If the R group is that of formula (2) given here-above, the hydrating compound according to the invention is a monosulfoxide of the following type:

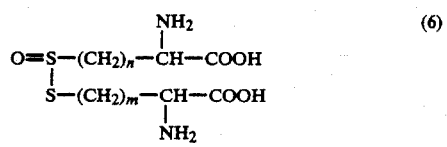

of which an example is supplied by the cystine monosulfoxide corresponding to formula (6) in which $n=m=1$.

Likewise, when the R group corresponds to the formula (3), the softening agent is a disulfoxide:

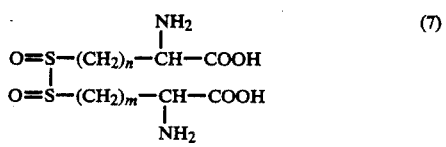

represented in particular by the cystine disulfoxide, i.e. body (7) with $n=m=1$.

In the case where R is an α-amino-acid group, sulfur-free, according to (3'), the product according to the invention is the sulfoxide:

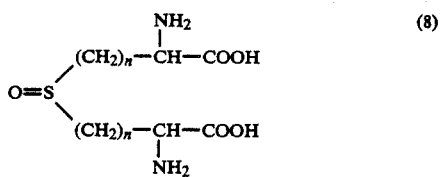

which may be illustrated by the example of cystathionine sulfoxide, the compound of formula (8) with $n=2$ and $m=1$.

From the above, it may be seen that the products according to the present invention are compounds readily accessible on an industrial basis.

Given the solubility of these products, they may be used for the applications mentioned herein-above, in an aqueous solution as well as in organic solvents, or in oily or other emulsions. Moreover, thanks to their amphoteric character, these bodies are able to buffer the pH of the preparations containing them up to the desired value, and especially at pH values close to those of cutaneous pH.

By way of illustration, but without in any way limiting the scope of the invention, the following examples are described here-under of tests with cosmetic applications in view, to which the novel softening agents contribute appreciable improvement.

EXAMPLE 1

Reduction of combing stress

Steps are taken to determine the effect of 5% methionine sulfoxide aqueous solution on the behaviour of hair during combing. In order to do this, a lock of hair is fixed by clamps to the arm of a balance; this lock is thereafter subjected to combing carried out mechanically, at a constant speed and from top to bottom. The maximum force is noted, as registered on the arm of the balance by the passage of the comb.

Three tests were carried out each with a lock of hair taken from the same head of hair; before the test, each lock was washed with a 1% sodium lauryl-sulfate aqueous solution, the rinsed with distilled water, dried and combed.

Whilst being kept together, in such a way as to avoid entangling the hair, the three locks were subjected to, with the same maximum force, a liquid treatment, followed by drying and conditioning, during 24 hours, in a 65% relative humidity atmosphere.

Set out below are the combing stresses found after the different treatments:

| Treatment | Stress in G |
|---|---|
| A - immersion in distilled water | 450 |
| B - immersion in a 5% methionine sulfoxide aqueous solution | 40 |

It can be seen that the action of methionine sulfoxide (B) has the effect of reducing at least to one tenth the combing stress presented by the hair which was treated simply with distilled water (A).

EXAMPLE 2

Determination of the hydration power of methionine sulfoxide

This determination is realised by measuring the hydration of the gelatine, in a way known per se.

Inside a ground tube, a 5 mm thick gelatine membrane hydrated at 80% is transversally fixed. With the aid of this tube, an Erlenmeyer containing water is sealed, and the assembly is left to reach its humidity balance at 35° C. during 24 hours. The tube is then tared and on the upper face of the gelatin, a determined weight of the solution whose hydration power is to be studied is placed. The tube is then replaced on the Erlenmeyer, in such a way as to seal it, and left to rest during 24 hours at 35°.

By the final weighing of the tube, taking into account the tare and the weight of the solution used, it is possible to find the quantity of water retained by the gelatin due to the action of the wetting agent.

The results are expressed in % by weight of water retained by the gelatin.

The tests were carried out with 5% solutions of different bodies used comparatively with methionine sulfoxide and, lead to the following results:

| | |
|---|---|
| Methionine sulfoxide | 15.2% |
| Lactic acid | 15.2% |
| Amniotic liquid | 11.9% |
| PCA Na | 11.4% |
| Sorbitol | 10.7% |
| Na Lactate | 10.6% |

| | -continued | |
|---|---|---|
| Urea | | 8.9% |
| Na Glycinate | | 7.8% |
| Glycerine | | 6.9% |
| Allantoine | | nil. |

These results show that methionine sulfoxide and lactic acid have an equivalent hygroscopic power. The results of evaluations carried out in Example 3 will show that the hydrating effect on skin of methionine sulfoxide is superior to that of lactic acid, due to an improved penetration of sulfoxide.

EXAMPLE 3

Evaluation of the hydrating effect on human skin by measuring cutaneous impedance The determination of the degree of hydration was determined by the E. CLAR method (Society of Cosmetic Chemists of Great Britain IISC Congress 1979) which consists in measuring the cutaneous impedance under weak frequency; it is known that in these conditions only the corneum stratum is involved and that the impedance diminishes with the hydration of the superficial layers of the skin.

On the forearm of 10 persons, three zones A, B and C are defined, of which the impedance is measured at 25° C. in a 50% relative humidity atmosphere under a frequency of 15 Hz, with platinum electrodes and an electrolytic liquid constituted by a mixture of polyethylene glycol having a molecular weight of 400 and physiological serum the composition of which is adjusted in order to be in balance with the ambient humidity; i.e. $T_0$ the value obtained in $K\Omega$ for each of the zones.

Thereafter, to zones A, B and C are applied the creams containing the products to be studied in such a way as to form a film of 10 microns on the surface of the skin after a gentle massage.

The application of the products was carried out in the following way:

to zone A: the reference sample cream was applied (product free); it is of the oil in water type;

to zone B: the same reference sample cream was applied to which had been added 10% lactic acid;

to zone C: the reference sample cream was applied to which had been added 7% methionine sulfoxide.

Twenty minutes after spreading of each of the creams, a system of electrodes was applied to the zones in question, and a measurement of the value $T_{20}$ (in $K\Omega$) was made.

Fifteen minutes after this measurement (i.e. 35 minutes after the beginning of the application) a further identical measurement was taken giving a value $T_{35}$ (in $K\Omega$).

The results of $T_0$, $T_{20}$ and $T_{35}$ are included in the table here-under, and the drop in impedance provoked by the application of the cream after 20 minutes i.e. $T_{20}-T_0$ and after 35 minutes, i.e. $T_{35}-T_0$ is also indicated. Also calculated and listed in the table here-under are the differences between the drop in impedance provoked by the creams containing the products, and the sample reference cream: i.e. $\Delta 20$ and $\Delta 35$ these differences for each of the creams containing the products.

| ZONE A | | ZONE B | | ZONE C | |
|---|---|---|---|---|---|
| Without cream | Sample reference cream | Without cream | Sample reference cream + 10% Lactic acid | Without cream | Sample reference cream + 7% methionine sulfoxide |
| $T_0$ 375.6 | $T_{20}$ 326 $T_{35}$ 273 | $T_0$ 414.5 | $T_{20}$ 350 $T_{35}$ 300.7 | $T_0$ 400 | $T_{20}$ 338 $T_{35}$ 278.7 |
| $T_{20} - T_0$ −49.5 | $T_{35} - T_0$ −102.5 | $T_{20} - T_0$ −64.5 | $T_{35} - T_0$ −113.8 | $T_{20} - T_0$ −62 | $T_{35} - T_0$ −121.3 |
| | | $\Delta 20$ l 15 | $\Delta 35$ l 11.3 | $\Delta 20$ m 12.5 | $\Delta 35$ m 18.8 |

The results listed in this table indicate the improved properties of methionine sulfoxide, as a skin hydrating product, with regard to products already known; in fact, although the value of $\Delta 20$ m is slightly lower than the value of $\Delta 20$ l, the value of $\Delta 35$ m is higher than $\Delta 35$ l and $\Delta 35$ l is lower than $\Delta 20$ l.

These results show that the methionine sulfoxide continues to diffuse and fix itself in the corneum stratum from 20 minutes onwards, whereas in the same conditions a cream containing lactic acid does not diffuse after 20 minutes.

The effect of methionine sulfoxide is even more noticeable with respect to lactic acid, a most effective, known hydrating agent, than when the latter was used in a stronger concentration, 10% against 7% only of methionine sulfoxide.

Naturally, this invention is in no way confined to the Examples and embodiments described above; many variant forms are possible for those skilled in the art, depending on applications, and without any departure from the spirit of the invention.

What is claimed is:

1. In a method of hydrating a keratinic formation by applying a composition comprising an active hydrating agent and a carrier therefore to such formation, the improvement which comprises employing, as active hydrating agent, an alpha-amino acid sulfoxide of the formula

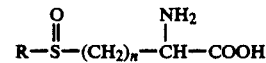

in which n is an integer from 1 to 4, R is a $C_{1-6}$ alkyl or alkenyl radical,

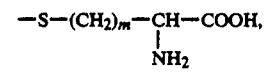

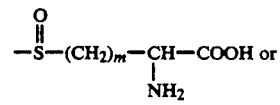

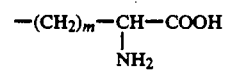

wherein m is an integer from 0 to 4 in an amount of 5-10% of said composition.

2. The method of claim 1 wherein R is a $C_{1-4}$ alkyl or alkenyl radical.

3. The method of claim 1 wherein R is

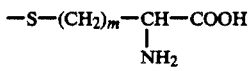

or

-continued

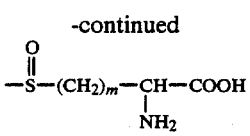

in which m is 1 to 4.

4. The method of claim 1 wherein R is

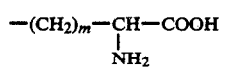

in which m is 1 to 4 and different from n.

5. The method of claim 1 in which said alpha-amino acid sulfoxide is methionine sulfoxide.

6. The method of claim 1 wherein said alpha-amino acid is cystine mono- or di-sulfoxide, cystathionine sulfoxide or an alkyl derivative of cysteine sulfoxide.

* * * * *